(12) United States Patent
Yetik

(10) Patent No.: US 9,770,167 B2
(45) Date of Patent: Sep. 26, 2017

(54) ILLUMINATED LENS APPARATUS

(71) Applicant: Huseyin Yetik, Istanbul (TR)

(72) Inventor: Huseyin Yetik, Istanbul (TR)

(73) Assignee: Huseyin Yetik, Istanbul (TR)

( * ) Notice: Subject to any disclaimer, the term of this patent is extended or adjusted under 35 U.S.C. 154(b) by 0 days.

(21) Appl. No.: 14/912,699

(22) PCT Filed: Apr. 18, 2014

(86) PCT No.: PCT/TR2014/000121
§ 371 (c)(1),
(2) Date: Feb. 18, 2016

(87) PCT Pub. No.: WO2015/034447
PCT Pub. Date: Mar. 12, 2015

(65) Prior Publication Data
US 2016/0220111 A1    Aug. 4, 2016

(30) Foreign Application Priority Data

Sep. 9, 2013   (TR) .............................. a 2013 10585

(51) Int. Cl.
| A61B 3/00 | (2006.01) |
| G02C 7/02 | (2006.01) |
| A61B 3/10 | (2006.01) |
| A61B 3/14 | (2006.01) |
| A61B 3/125 | (2006.01) |
| A61B 3/15 | (2006.01) |

(Continued)

(52) U.S. Cl.
CPC ............ *A61B 3/125* (2013.01); *A61B 3/0008* (2013.01); *A61B 3/15* (2013.01); *A61B 90/30* (2016.02); *A61B 2090/306* (2016.02); *A61F 9/00736* (2013.01)

(58) Field of Classification Search
CPC .... G02C 5/00; G02C 7/02; G02C 7/04; A61B 3/125; A61B 90/30; A61B 2090/306; A61B 3/117; A61B 3/103; A61B 3/1208; A61B 3/14; A61B 3/113; A61B 3/024; A61B 3/1015
USPC ....... 351/219, 200, 218, 205, 209, 210, 222, 351/246, 41, 159.01, 159.02, 160 R
See application file for complete search history.

(56) References Cited

U.S. PATENT DOCUMENTS

| 3,630,602 A | 12/1971 | Herbert |
| 3,954,329 A | 5/1976 | Pomerantzeff |

(Continued)

FOREIGN PATENT DOCUMENTS

WO    WO 95/13768 A1    5/1995

OTHER PUBLICATIONS

International Search Report in corresponding PCT Application No. PCT/TR2014/000121, Nov. 12, 2014.

*Primary Examiner* — Dawayne A Pinkney
(74) *Attorney, Agent, or Firm* — Leason Ellis LLP

(57) ABSTRACT

The present invention relates to an illuminated lens apparatus (10) placed on the eye wall and comprising a hollow base (11), a fixed lens (13) placed inside said hollow section and a handle (14) connected to the base (11). Said illuminated lens apparatus (10) is characterized in comprising a ring (12) provided in such a manner to enclose the base (11) upper surface and at least one bushing (20) configured on said ring (12) in such a manner to enable positioning of illumination probe (30) therein.

10 Claims, 2 Drawing Sheets

(51) Int. Cl.
*A61B 90/30* (2016.01)
*A61F 9/007* (2006.01)

(56) References Cited

U.S. PATENT DOCUMENTS

| | | | | |
|---|---|---|---|---|
| 4,553,824 | A * | 11/1985 | Abe | A61B 3/117 |
| | | | | 351/219 |
| 5,537,164 | A * | 7/1996 | Smith | A61B 3/117 |
| | | | | 351/205 |
| 6,221,028 | B1 * | 4/2001 | Lieberman | A61B 3/14 |
| | | | | 351/200 |
| 2012/0099077 | A1 | 4/2012 | Abt | |

* cited by examiner

ILLUMINATED LENS APPARATUS

CROSS-REFERENCE TO RELATED PATENT APPLICATIONS

This application is a U.S. National Phase Application under 35 U.S.C. §371 of International Patent Application No. PCT/TR2014/000121, filed Apr. 18, 2014, and claims the priority of Turkish Application No. 2013/10585, filed Sep. 9, 2013, all of which are incorporated by reference in their entireties. The International Application was published on Mar. 12, 2015 as International Publication No. WO 2015/034447 A1.

TECHNICAL FIELD

The invention relates to an illuminated lens apparatus developed for fixation of the illumination probe, which is used for illumination of the intraocular area without the need of inserting thereof into the eye, in the eye surgeries, particularly in vitreoretinal surgery operations.

PRIOR ART

Illumination of the intraocular area is of paramount importance during eye surgeries, particularly in vitreoretinal surgery operations. In particular, the surgeon must see the vitreus, retina, choroid and optic nerve structures located within the area under surgery. There are two key elements for rendering the intraocular area visible. The first key element is a lens rendering the intraocular area visible, and the second element is illumination of the intraocular area.

There are two distinct apparatuses for illumination of the intraocular area. The first apparatus is a fiber optic illumination probe held by the surgeon during the surgery. Illumination with probe causes the surgeon to perform the surgery with one hand as s/he continuously holds the illumination probe with the other hand during the surgery. Therefore, such illumination system necessitates assistance to the surgeon when the surgeon needs his/her second hand. The second method, on the other hand, is the chandelier illumination system fixed to two holes drilled on the ocular surface and remains suspended in the ocular surface during the surgery. The disadvantage of the chandelier illumination system is the cut made on the ocular surface at the beginning of the operation. On the other hand, as the chandelier illumination probe position is stationary, the shadows of the apparatus might cast onto undesired locations, in particular on the surgery area during the operation. Both systems prove to be inadequate for optimum illumination.

In the patent application with WO2010129775A1 reference number, a lens configuration used for illuminating the bottom zone of the intraocular area is described. Said apparatus contains a lens provided in front of the contact lens adhering to the ocular surface. The lens enables complete illumination of the intraocular area by distributing the light rays coming from a light source positioned behind the lens. However, said apparatus is used for diagnosing the eye diseases and it is not suitable for use in the eye surgeries due to its structure.

In conclusion, the prior art mentioned above necessitates an improvement in the concerned technical field.

BRIEF DESCRIPTION OF THE INVENTION

The present invention relates to an illuminated lens apparatus in order to eliminate the disadvantages mentioned above and bring new advantages to the applicable technical field.

The objective of the invention is to propound an illuminated lens apparatus ensuring fixation of the illumination units used for illuminating the intraocular area during the eye surgeries and providing easier and more effective illumination to the desired operative field.

Another objective of the invention is to propound an illuminated lens apparatus enabling the surgeon to use both hands during the eye surgery.

In order to fulfill all objectives mentioned above and to be understood from the detailed description provided herein, the present invention relates to an illuminated lens apparatus placed on the eye wall and comprising a hollow base, a fixed lens placed inside said hollow section and a handle connected to the base. Said illuminated lens apparatus comprises a ring provided in such a manner to enclose the base upper surface and minimum one bushing configured on said ring in such a manner to enable positioning of illumination probe therein.

A preferred embodiment of the invention comprises al least one retainer section ensuring connection of said bushing on the ring.

Another preferred embodiment of the invention comprises a hinge connected to the bushing over the retainer section in order to protect the angular positions of the bushing within said retainer section.

Another preferred embodiment of the invention is that the first bushing provided on the ring is positioned in the same alignment with the intersection point of the handle and the base.

Another preferred embodiment of the invention is that there are multiple bushings.

Another preferred embodiment of the invention is that the bushings are positioned on the ring with equal intervals.

Another preferred embodiment of the invention comprises one bushing, wherein said bushing can rotate on the ring completely by 360 degrees. The ring is provided with rail structure in order to enable such bushing movement.

Another preferred embodiment of the invention is that the fiber optic illumination light illuminates underneath the lens by passing all along through the handle.

Another preferred embodiment of the invention is that the apparatus contains a fluid terminal provided on the handle and a channel extending towards the base following the fluid terminal and through which an irrigation fluid, which continuously washes and cleans the cornea and lens interface, thus ensuring continuity of the image, flows.

Another preferred embodiment of the invention is that the apparatus contains a curvilinear wall in such a manner to consummate, in form, the curvilinearity of the eye wall of the base.

REFERENCE NUMBERS ON THE DRAWINGS

10 Illuminated Lens Apparatus
  11 Base
    111 Curvilinear wall
  12 Ring
    121 Retainer Section
  13 Lens
  14 Handle
    141 Fiber Optic Cable 142 Fluid Terminal
20 Bushing
21 Hinge
30 Light Probe
31 Terminal

DETAILED DESCRIPTION OF THE INVENTION

In this detailed description, the novelty of the invention and its preferred embodiments are described only for a better understanding of the subject matter without any limiting effect. Accordingly, an illuminated lens apparatus (10) on which the illumination probes (30), which are used for illumination of the intraocular area, are placed in the eye surgeries, particularly in vitreoretinal surgery operations, and the elements forming an illuminated lens apparatus (10) are described herein.

Figure 1:
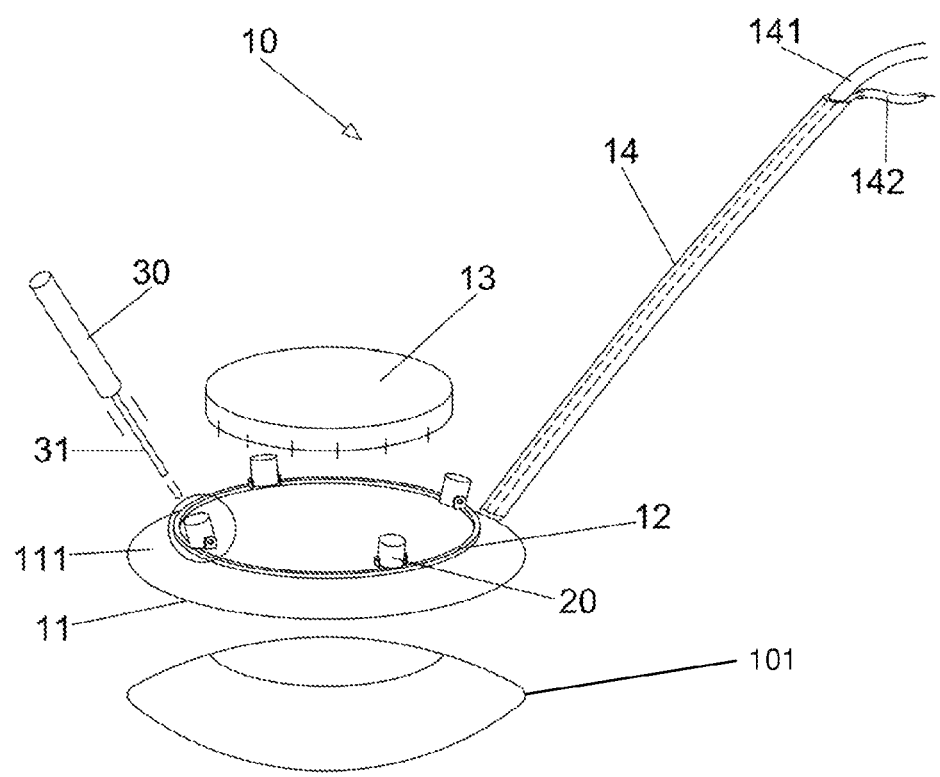
FIG. 1 illustrates the general view of the illuminated lens apparatus.

FIG. 1 illustrates the perspective view of the illuminated lens apparatus (10). Illuminated lens apparatus (10) has a base (11) fitting to the eye surface and comprising curvilinear wall (111) in compliance with the curvilinear surface of the eye. The base (11) is circular in form, and is hollow. There is a clear lens (13) placed within this hollow section. The lens (13) is placed in such a manner to fill the hollowness inside the base (11) in form. The lens (13) neutralizes the eye optics and enables visualization of the fundus oculi. There is a ring (12) provided on the upper wall of the base (11). The lens is fixed at the center of said ring. There is a handle (14) in connection with the base (11), enabling grapping of the illuminated lens apparatus (10) by the user. There is a fiber optic cable (141) provided in the handle (14). There is a fluid terminal (142) provided on the handle (14). A channel is provided following said fluid terminal which, allows circulation of a fluid around the fiber optic cable (141). Irrigation fluid flows through said channel (not shown in the figure). The irrigation fluid passes through the void between the lens (13) and the base (11), and reaches to the cornea of the eye. By virtue of the continuous irrigation fluid flow, the lens (13)—cornea interface shall not only be maintained clean, but also said fluid shall cover the potential void between mutual contact surfaces of said cornea and lens (13) and ensures that both surfaces act as a monolithic structure, thus enabling achievement of a clear image.

Figure 2:
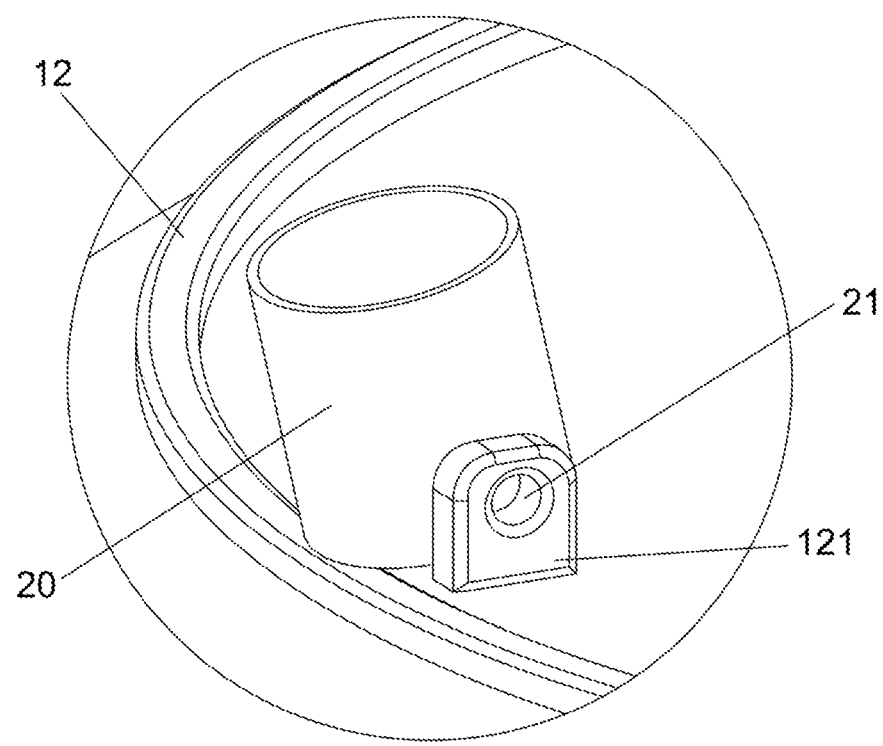
FIG. 2 illustrates the connection detail.

FIG. 2 illustrates the detailed view of the ring (12) section. The ring (12) contains multiple retainer sections (121) and bushing (20) like configurations placed inside said retainer sections (121). The bushings (20) are connected to the retainer sections (121) by means of hinges (21). At a standard connection, the bushings (20) are fixed on the ring (12) with 45° angle. However, the angle of bushings (20) on the ring (12) might be modified using hinges (21) should any need arises. The bushing (20) position is maintained by means of retightening the hinges (21), which are loosened at the beginning of the operation, after bringing the bushing (20) to the desired position on the ring (12), or the apparatus is used by changing the angle dynamically by the assistant constantly during the surgery. There are four bushings (20) placed on the ring (12) with equal intervals with handle (14) being the origin.

The number of bushings (20) available on the ring (12) might be varied by positioning additional bushings with equal distance in between depending on the requirement. For instance, the angle between the bushings where there are two bushings (20) on the ring (12) is 180°; said angle is 120° if there are three bushings (20), and 90° if there are four bushings (20). There is a terminal (31) ensuring installation of the light probe (30) within the bushing (20) and maintaining its position. The terminal (31) also performs illumination function.

The illuminated lens apparatus (10) is positioned on the eye wall (101) by means of the handle (14). Irrigation fluid is supplied to the eye surface during the operation through the connection made to the fluid terminal (142). The lens (13) is positioned above the cornea of the eye. Then the light probe (30) is installed within the bushing (20) considered suitable by the surgeon depending on the position of the zone to be illuminated from the terminal (31). Adequate number of light probes (30) is connected to the bushings (20) depending on the requirements. When operated, the light probe (30) passes the retina layer and enables illumination of the intraocular area of the eye. If required or if the operation zone is modified, the surgeon or his/her assistant can modify the angle of the light probe, that is to say, the position of the bushing containing such light probe, or might change the light probe between the bushings. In this manner, different zones within the eye might be illuminated in accordance with the requirements.

In alternative embodiments of the invention, the ring (12) provided on the base (11) is configured in the form of rail. In this manner, one bushing (20) provided on the ring (12) can be moved 360° on the ring and its position can be fixed at any desired position. Thus, one bushing (20) shall be sufficient for illumination of the desired zones within the eye. In another alternative embodiment, dedicated light probes (30) or illumination elements peculiar to the illuminated lens apparatus (10) can be designed. By virtue of the illumination elements in smaller sizes, the surgeons can perform operation more comfortably.

The invention claimed is:

1. An illuminated lens apparatus (10) placed on an eye wall to illuminate light over a cornea of an eye, comprising:
   a hollow base (11);
   a fixed lens (13) placed inside said hollow base;
   a handle (14) connected to the base (11);
   a ring (12) to enclose the base (11) having an upper surface and at least one bushing (20) configured on said ring (12) to position at least one illumination probe (30) therein, wherein the ring has a center and wherein the fixed lens (13) is placed at the center of said ring (12), wherein the bushing (10) is adapted to tilt any angle and locked at an angle using a retainer section (121);
   a fluid terminal (142) provided on the handle (14); and
   a fiber optic light cable (141) passes through the fluid terminal (142), wherein the illumination probe (30) and the fiber optic light cable (141) illuminates light on the fixed lens.

2. The illuminated lens apparatus (10) according to claim 1, wherein the illuminated lens apparatus comprises minimum one retainer section (121) ensuring connection of said bushing (20) on the ring, wherein the retainer section is adapted to fix the bushing in different angles.

3. The illuminated lens apparatus according to claim 2, wherein the illuminated lens apparatus comprises a hinge (21) connected to the bushing (20) over the retainer section (121) to protect the bushing (20) in different angle within said retainer section (121), wherein the illumination probe (30) is adapted to tilt any angle and provide illumination in any angle, wherein the illumination probe (30) tilts any angle according to the angle of bushing (20).

4. The illuminated lens apparatus (10) according to claim 2, wherein the first bushing (20) provided on the ring (12) aligns with an intersection point of the handle (14) and the base (11).

5. The illuminated lens apparatus (10) according to claim 1, wherein the illuminated lens apparatus comprises multiple bushings (20), wherein each bushing (20) is adapted to receive one illumination probe (30).

6. The illuminated lens apparatus (10) according to claim 5, wherein (i) the bushings (20) are positioned on the ring (12) with equal intervals, (ii) the bushings (20) are positioned on the ring (12) with an angle 180° when two bushing are positioned on the ring (12), (iii) the bushings (20) are positioned on the ring (12) with an angle 120° when three bushing are positioned on the ring (12) or (iv) the bushings (20) are positioned on the ring (12) with an angle 90° when four bushing are positioned on the ring (12).

7. The illuminated lens apparatus (10) according to claim 2, wherein the illuminated lens apparatus comprises a channel extending towards the base (11) following the fluid terminal (142) and through which a surgery fluid flows.

8. The illuminated lens apparatus (10) according to claim 2, wherein the illuminated lens apparatus comprises a monolithic channel extending towards the base (11) following the fluid terminal (142) and through which the fiber optic light cable passes.

9. The illuminated lens apparatus (10) according to claim 1, comprising a curvilinear wall (111) in such a manner to consummate, in form, the eye wall of the base (11).

10. The illuminated lens apparatus (10) according to claim 1, wherein said ring (12) is configured in a rail form that enables 360° movement of the bushing (20) on the fixed lens.

* * * * *